United States Patent [19]

Endres et al.

[11] Patent Number: 4,739,088

[45] Date of Patent: Apr. 19, 1988

[54] PROCESS FOR THE PREPARATION OF AMIDOSILANES

[75] Inventors: Robert Endres, Bergisch-Gladbach; Armand de Montigny, Leverkusen, both of Fed. Rep. of Germany

[73] Assignee: Bayer Aktiengesellschaft, Leverkusen-Bayerwerk, Fed. Rep. of Germany

[21] Appl. No.: 824,463

[22] Filed: Jan. 31, 1986

[30] Foreign Application Priority Data

Feb. 12, 1985 [DE] Fed. Rep. of Germany ....... 3504644

[51] Int. Cl.[4] .............................. C07F 7/10; C07F 7/18
[52] U.S. Cl. .................................................... 556/411
[58] Field of Search ......................................... 556/411

[56] References Cited

U.S. PATENT DOCUMENTS 3,776,933  12/1973  Toporcer et al. .................... 556/411
4,252,977   2/1981  Mitchell et al. ..................... 556/411

OTHER PUBLICATIONS

Title: Chemical Abstracts. Article: "Silicon-Containing Amides, IV. Reaction of Sodium Ethylacetamide with Methyldialkoxychloremethylsilanes", author: Maslii et al dated 1968, Vol and date of magazine: vol. 71 dated Sep. 1, 1969.

Primary Examiner—Paul F. Shaver
Attorney, Agent, or Firm—Connolly & Hutz

[57] ABSTRACT

Highly pure amidosilanes of the formula

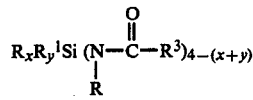

wherein

R is alkyl having 1 to 18 carbon atoms, cycloalkyl having 5 to 18 carbon atoms, alkenyl having 2 to 18 carbon atoms and aryl having 6 to 18 carbon atoms, $R^1$ is alkoxy having 1 to 18 carbon atoms, $R^2$ and $R^3$ each independently of one another are alkyl having 1 to 18 carbon atoms or aryl having 6 to 18 carbon atoms, x is 1, 2 or 3, y is 0, 1 or 2, with the sum of x and y being 1 to 3, are produced by reacting an alcohol-free suspension of alkali metal salts or organic amides with organosilanes wherein said salts of amides are prepared by reacting a compound of the formula

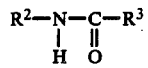

with an alcoholic solution of an alkali metal alcoholate in inert organic solvents and the removing alcohol from the reaction mixture by distillation, and said organosilanes are of the formula

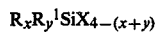

wherein X is a halogen or a carboxylate moiety having 1 to 18 carbon atoms, with the reaction being carried out with the exclusion of moisture in inert organic solvents.

8 Claims, No Drawings

PROCESS FOR THE PREPARATION OF AMIDOSILANES

BACKGROUND OF THE INVENTION

The present invention relates to a process for the preparation of amidosilanes. These compounds have hitherto been prepared from organochlorosilanes and organic amides in the presence of a tertiary amine to capture liberated hydrochloric acid. Such a process is described in, for example, U.S. Pat. No. 2,876,234, U.S. Pat. No. 3,488,371 and German Published Specification No. 1,224,039. This process frequently leads to amidosilanes which, after removal of the solvent, are still so impure that they have to be purified by distillation or a thin-layer method. Large amounts of trialkylammonium salts are additionally produced, and their processing is likewise elaborate.

According to U.S. Pat. No. 3,776,933 and German Published Specification No. 2,319,818, amidosilanes can also be obtained from the alkali metal salts of the organic amides and organohalogenosilanes when alkali metals, such as sodium, finely divided in toluene are heated to reflux and excess amide is reacted therewith, accompanied with hydrogen being formed. This process has the disadvantage that the use of sodium metal is problematical concerning technical handling and that the formation of the metallated amide takes place slowly with the amide being exposed to detrimental thermal stress.

Thus, it is possible for N-benzoylbenzamidines to be formed irreversibly from

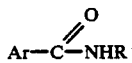

on heating in toluene, and these unavoidably lead to product impurities.

Use of alkali metal has the additional disadvantage that, for safety reasons, even the smallest residues of unreacted metal must be completely removed before further processing of the reaction mixture.

The object of the present invention was to eliminate the disadvantages which have been mentioned.

BRIEF DESCRIPTION OF THE INVENTION

The present invention relates to a process for the preparation of aminosilanes by reacting a suspension of alkali metal salts of organic amides with organosilanes wherein the amide salts have been prepared by reacting an organic amide with an alcoholic solution of alkali metal alcoholate in the presence of an inert organic solvent with alcohol being removed from the reaction mixture.

DETAILED DESCRIPTION OF THE INVENTION

The invention relates to a process for the preparation of amidosilanes of the formula

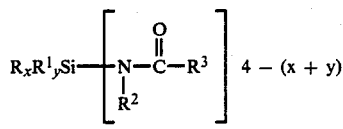

R is alkyl, cycloalkyl, alkenyl and aryl,
$R^1$ is alkoxy,
$R^2$ and $R^3$ are, independently of one another, alkyl, aryl,
x is 1, 2 or 3;
y is 0, 1 or 2; and the sum of x and y is 1 to 3,
by reaction of suspensions of alkali metal salts or organic amides of the formula

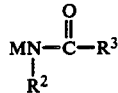

where M is alkali metal, and organosilanes of the formula $$R_x R_y{}^1\!-\!Si\!-\!X_{4-(x+y)}$$

wherein X is halogen or a carboxylate moiety with 1 to 18 carbon atoms, and x and y are as defined above the reaction being carried out with exclusion of moisture in inert organic solvents, which is characterised in that the alkali metal salts of the organic amides are prepared by reaction of their corresponding amides in inert organic solvents with alcoholic solutions of alkali metal alcoholate, with alcohol being removed quantitatively from the reaction mixture by distillation.

R in the amidosilane formula can be an aliphatic moiety from $C_1$ to $C_{18}$, preferably $C_1$ to $C_3$ alkyl, a cycloaliphatic moiety from $C_5$ to $C_{18}$, preferably cycloalkyl from $C_5$ to $C_6$, an aromatic moiety from $C_6$ to $C_{18}$, preferably phenyl, an olefinic moiety from $C_2$ to $C_{18}$, preferably alkenyl from $C_2$ to $C_6$, each of which is unsubstituted or substituted with additional moieties which do not react with alkali metal alcoholate solutions under the reaction conditions of the process of this invention. Most preferably, R is methyl.

$R^1$ is an alkoxy group of $C_1$ to $C_{18}$.
$R^1$ is preferably ethoxy.
$R^2$ and $R^3$ are alkyl groups from $C_1$ to $C_{18}$ and/or aromatics, and their substitution products which do not react with alkali metal alcoholate solutions under the conditions mentioned. It is also possible for $R^2$ and $R^3$ together to be an alkylene moiety of 3 to 6 carbon atoms whereby $R^2$ and $R^3$ together form a ring (lactams).

$R^2$ and $R^3$ are preferably methyl, ethyl and phenyl.
M is an alkali metal with sodium being particularly preferred for economic reasons.

X is Cl, Br or I, and a carboxylate having 1 to 18 carbons, and preferably acetate or propionate.

Particularly suitable solvents for the amides are substances which boil higher than the alcohols used and are inert toward the alkali metal alcoholates, such as, for example, toluene, xylene, di-n-propyl ether and n-octane.

Toluene is particularly preferably used because of its very good solvent capacity for organic amides.

Particularly suitable solvents for the alcoholates are methanol, ethanol and i-propanol. The boiling point differences and the azeotropic characteristics of these binary systems are listed in the table which follows:

| Alcohol (boiling point) | Solvent as 2nd component (boiling point) | Binary azeotrope | |
|---|---|---|---|
| | | (boiling point) | Proportion of the 2nd component |
| Methanol | Toluene | 63.8° C. | 31% by weight |

| Alcohol (boiling point) | Solvent as 2nd component (boiling point) | Binary azeotrope | |
|---|---|---|---|
| | | (boiling point) | Proportion of the 2nd component |
| (64.7° C.) | (110.8° C.) | | |
| Methanol (64.7° C.) | Di-n-propyl ether (90.4° C.) | 63.8° C. | 28% by weight |
| Methanol (64.7° C.) | n-Octane (124.8° C.) | 62.8° C. | 32.5% by weight |
| Ethanol (78.3° C.) | Toluene (110.8° C.) | 76.7° C. | 32% by weight |
| Ethanol (78.3° C.) | Di-n-propyl ether (90.4° C.) | 74.4° C. | 56% by weight |
| Ethanol (78.3° C.) | n-Octane (124.8° C.) | 77.0° C. | 22% by weight |
| i-Propanol (82.5° C.) | Toluene (110.8° C.) | 81.3° C. | 21% by weight |
| | n-Octane (124.8° C.) | 81.6° C. | 16% by weight |

The ideal solvent system for the metallation of the organic amides is toluene (good solvent properties, no peroxide formation compared with the ethers) and methanol (reasonably priced commercially available 30% by weight methanolic sodium methanolate solution). The boiling point difference for this system is 46.1° C. under atmospheric pressure; the azeotropic point is at 63.8° C. and 31% by weight of toluene, that is to say the azeotrope is enriched with 69% by weight of the more volatile component methanol. Quantitative removal by distillation (methanol < 0.1% by weight in the remaining solution) is necessary in order to prevent the formation of undesired methoxysilanes, in the subsequent reaction with the organosilanes. Since, under atmospheric pressure, the temperature at the head of the column rises to 110.8° C. and the bottom temperature rises to about 130° to 150° C., it is advisable to reduce the bottom temperature (distillation pot) to 60° to 70° C., because of heat sensitivity of the organic amides, especially the aromatic amides, with the formation of N-benzoylbenzamidines or analogous substituted derivatives, which has already been mentioned.

Temperature reduction is achieved by reduction of the pressure during the azeotrope/toluene temperature jump. In order to avoid an excessive decrease of the condensation temperature of the distillate, it is advisable to choose a pressure allowing to operate slightly above 60° C.

If the alkali metal alcoholate suspension remaining after removal of the azeotrope by distillation and the incipient distillation of the higher boiling component becomes too viscous, it is possible to add further anhydrous higher boiling component. The rate of stirring is adjusted so that the mixture remains homogeneous.

The addition of the organohalogenosilane in the 2nd stage results in an exothermic reaction. Cooling must be carried out where necessary to maintain the preferred temperature of 60° to 80° C. for the formation of the amidosilanes.

The reaction time is between 1 and 12 hours, 3 to 5 hours being preferred and being adequate for quantitative conversion when mixing is thorough.

Because of their ready availability and for economic reasons, organochlorosilanes of the formula

are used as the organosilanes.

The maximum value of $x+y$ should not exceed 3 so that a reaction takes place. When $x=2$ and $y=0$ or 1, the resulting chain-extenders are of the following type

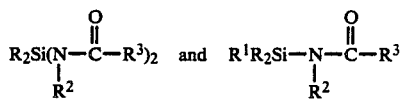

R is alkyl, cycloalkyl, alkenyl and aryl,
$R^1$ is alkoxy,
$R^2$ and $R^3$ are independently of one another, alkyl and aryl which, as a rule, increase the elongation at break of highly elastic organopolysiloxane compositions.

In the cases where $x=1$ and $y=0$ to 2, crosslinkers of the following types

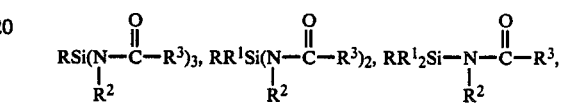

are obtained, with which it is possible to prepare organopolysiloxane compositions for shaping and sealing.

In the case where $y=0$ and $x=3$, the silanes obtained regulate the chain lengths of polymers.

The amidosilanes synthesised by the claimed process are, after removal of the alkali metal halide by filtration, present in the solvent which, because of the heat-sensitivity of the final products, is removed under mild conditions under an appropriate vacuum.

The present process according to the invention has the advantage that the final products are produced, after removal of the solvent in vacuo, so pure that distillation of the product as a purification process is no longer necessary, and for the very first time economic preparation of heat-sensitive pure amidosilanes is possible.

The examples which follow are intended to explain the invention without limitation thereto:

EXAMPLE 1

Di(N-ethylacetamido)methylethoxysilane 176 g of N-ethylacetamide (99% pure, 2 moles) were dissolved in 2000 g of anhydrous toluene in a vacuum-tight 5 l stirred vessel with a packed column (1000 × 60 mm, 80 mm Berl saddles), efficient condenser, nitrogen inlet and multiple vacuum receiver in place, and 423.5 g of methanolic sodium methanolate solution (25.5% strength, 2 moles) were added at room temperature, with stirring and exclusion of moisture. This resulted in a white suspension from which the methanol/toluene azeotrope was distilled out under atmospheric pressure, while stirring, at a head temperature of 64° C. After complete removal of the methanol (head temperature 110.8° C., GC check), the suspension was cooled to about 50° C. and, while stirring and cooling, 157 g of methylethoxydichlorosilane (99.3% pure, 0.98 mole) was added dropwise in such a manner that the bottom temperature did not exceed 70° C.; the mixture was then stirred at 70° C. for 3 h. After cooling the suspension to room temperature, it was filtered with exclusion of moisture (Seitz pressure filter, 4 bar of $N_2$, K 300 filter insert) and washed with 2×400 g of anhydrous toluene. The solvent was removed under 10 mbar, and 233.8 g of a pale yellow oily liquid were obtained in a yield of 97.6% of theory.

Approximately 20% strength solutions in CDCl₃ were prepared of the substance obtained and of the products in the examples which follow.

Chemical shift (ppm) relative to TMS in the ¹H NMR: a=0.53, b=1.17, c=2.07, d=3.27, e=3.83.

$$CH_3(CH_3-CH_2O)-Si-(N-\overset{\overset{O}{\|}}{C}-CH_3)_2$$
$$\phantom{CH_3(}a\phantom{H_3-}b\phantom{-C}e\phantom{H_2O)-Si-(}d\phantom{-}\underset{\underset{b\phantom{H_3}\ \ CH_3}{|}}{CH_2}\phantom{-C-CH}c$$

EXAMPLE 2

D-(N-methylpropionamido)methylethoxysilane

In the same apparatus as in Example 1, 174.9 g of N-methylpropionamide (99.6% pure, 2 moles) were dissolved in 2,500 g of anhydrous toluene and, at room temperature, 423.5 g of methanolic sodium methanolate solution (25.5% strength, 2 moles) were added. After complete removal of the methanol as in Example 1 and analogous reaction with 157 g of methylethoxydichlorosilane (99.3% pure, 0.98 mole), and after filtration and washing of the filter cake and removal of the solvent by distillation, 239.8 g of a pale yellow oily liquid were obtained in a yield of 98.1%.

¹H NMR (σ in ppm relative to TMS): a=0.33, b=1.20, c=2.33, d=2.83, e=3.77.

$$CH_3(CH_3-CH_2O)Si-(N-\overset{\overset{O}{\|}}{C}-CH_2-CH_3)_2$$
$$\phantom{CH_3(C}a\phantom{H_3-}b\phantom{-CH}e\phantom{2O)Si-(N}d\phantom{-}CH_3\phantom{-C-CH}c\phantom{-}b$$

EXAMPLE 3

N-Methylacetamidomethyldiethoxysilane 183.4 g of N-methylacetamide (99.5% pure, 2.5 moles) in 1.5 kg of anhydrous toluene were initially introduced into the apparatus of Example 1 and, at room temperature, 532.5 g of sodium methanolate solution (25.5% strength, 2.5 moles) were added. After quantitative removal of the methanol as in the previous examples, 434 g of methyldiethoxychlorosilane were added dropwise with stirring (97.1% pure, 2.5 moles) and the process was continued in analogy to Example 1. 499.7 g of a pale yellow oily liquid were obtained in a yield of 97.5%.

¹H NMR (σ in ppm relative to TMS): a=0.33, b=1.20, c=2.07, d=2.80, e=3.80.

$$CH_3(CH_3-CH_2O)_2-Si-N-\overset{\overset{O}{\|}}{C}-CH_3$$
$$\phantom{CH_3(C}a\phantom{H_3-}b\phantom{-CH_2O)_2-}e\phantom{Si-}\underset{d}{CH_3}\phantom{-C-}c$$

EXAMPLE 4

N-Phenylacetamidomethyldiethoxysilane

In the apparatus of Example 1, 338.9 g of N-phenylacetamide (99.7% pure, 2.5 moles) were dissolved in 1.5 kg of anhydrous toluene and, at room temperature, 829.3 g of sodium ethanolate solution (20.5% strength, 2.5 moles) were run in. The ethanol/toluene azeotrope was distilled out, while stirring, at a head temperature of 77° C. After complete removal of the ethanol (head temperature 110.8° C., GC check), the mixture was cooled to a bottom temperature of about 50° C. and, while stirring, 434 g of methyldiethoxychlorosilane were added dropwise (97.1% pure, 2.5 moles), and the mixture was stirred at 60° C. for 2 h. After cooling and filtration, the residue was washed twice with 500 g of toluene, and the solvent was removed from the filtrate in vacuo. A pale oily liquid was obtained in a yield of 96.7% (646 g).

Chemical analysis of N-phenylacetamidomethyldiethoxysilane:

|  | % C | % H | % N | % Si |
|---|---|---|---|---|
| Found: | 58.4 | 8.1 | 5.8 | 10.5 |
| Calculated: | 58.5 | 7.9 | 5.2 | 10.5 |

EXAMPLE 5

Tri(N-methylacetamido)methylsilane

In an apparatus according to Example 1, 132 g of N-methylacetamide (99.5% pure, 1.8 mole) were dissolved in 1.5 kg of toluene, and 380 g of sodium methanolate solution (25.5% strength, 1.8 mole) were added. After removal of the methanol by azeotropic distillation, 90 g of methyltrichlorosilane (99.4%, 0.6 mole) were added dropwise, within 30 minutes, to the suspension at 60° C., and the suspension was stirred at 70° C. for 3 h. After cooling of the mixture, it was worked up in analogy to Example 1. This resulted in a pale yellow oily liquid, which crystallised at room temperature, with a yield of 95%, corresponding to 147.6 g of product.

Chemical shift σ (ppm) in the ¹H NMR, relative to TMS: a=0.53, b=2.00, c=2.67.

$$CH_3-Si(N-\overset{\overset{O}{\|}}{C}-CH_3)_3$$
$$\phantom{CH_3-Si(}\underset{a}{|}\phantom{-C-CH_3)}$$
$$\phantom{CH_3-Si(}CH_3\phantom{-C-CH_3)}$$
$$\phantom{CH}a\phantom{_3-Si(N-}c\phantom{-CH_3)_}b$$

The amidosilanes of Examples 1 to 5 were each used as crosslinkers in the following recipe for a sealant:
61.5 parts by weight of hydroxyl-terminated polydimethylsiloxane, viscosity about 50,000 mPas (25° C.)
24.2 parts by weight of unreactive polydimethylsiloxane, viscosity about 1,500 mPas (25° C.)
4.0 parts by weight of crosslinker
9.5 parts by weight of Aerosil 130 CF (supplied by Degussa)
0.01 parts by weight of dibutyltin diacetate
On contact with atmospheric moisture, in each case the result was a moderately transparent, completely cured and highly elastic sealant.

EXAMPLE 6

Di(N-methylbenzamido)methylethoxysilane

In an apparatus according to Example 1, 405.5 g of N-methylbenzamide (3 moles) were dissolved in 2,400 g of anhydrous toluene at 65° C., and 642.2 g of sodium methanolate solution (25.24% strength, 3 moles) were run in. The methanol/toluene azeotrope was distilled out under reduced pressure (450 to 180 mbar) and a head temperature between 35° and 50° C. in such a manner that the bottom temperature was between 60° and 65° C. After a temperature jump of about 10° C., while continuing to maintain the bottom temperature constant a further approximately 100 g of distillate were removed until methanol was no longer detectable (GC check). Then 238.7 g of methylethoxydichlorsilane (99% pure, 1.485 mole) were added dropwise, and the mixture was cooled during this so that the bottom temperature did not exceed 70° C., and then the mixture was stirred at this temperature for 3 h.

The suspension was worked up as in Example 1. 503 g of a pale yellow oily liquid were obtained (95% yield).

$^1$H NMR ($\sigma$ in ppm relative to TMS): a=0.47, b=1.20, c=2.87, d=3.87, e=7.27, f=7.73.

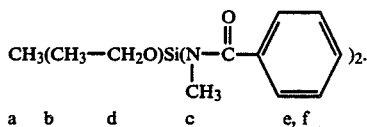

EXAMPLE 7

N-Methylbenzamidomethyldiethoxysilane

In a stirring and distillation apparatus according to Example 1, 202.8 g of N-methylbenzamide (1.5 mole) were dissolved in 1500 g of anhydrous toluene at 65° C., and 321.1 g of sodium methanolate solution (25.25% strength, 1.5 mole) were run in, the process was carried out in accordance with Example 6. Then 259.2 g of methyldiethoxychlorosilane (97% pure 1.49 mole) wer slowly added dropwise, and the bottom temperature was maintained at 70° C., and the mixture was then stirred at this temperature for 3 h. The working up was carried out in analogy to Example 1, and 388.5 g (97.5% yield) of a pale, slightly yellowish oily liquid were obtained.

$^1$H NMR ($\sigma$ in ppm relative to TMS): a=0.20, b=1.17, c=2.93, d=3.83, e=7.37, f=7.93.

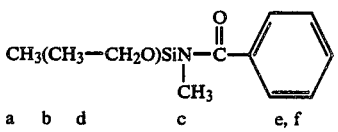

The crosslinkers of Examples 6 and 7 were used in the following recipe:
45.2 parts by weight of hydroxyl-terminated polydimethylsiloxane, viscosity about 50,000 mPas (25° C.)
19 parts by weight of unreactive polydimethylsiloxane, viscosity about 1500 mPas (25° C.)
5.5 parts by weight of ®Ti-chelane compound,
5.0 parts by weight of crosslinker, prepared in accordance with Example 6 or 7,
20 parts by weight of chalk,
5.5 parts by weight of silica (BET 150 m²/g)
0.5 part by weight of dibutyltin dilaurate.

The composition thus prepared resulted, on painting onto a glass plate in moist air, in a white, completely cured sealant.

EXAMPLE 8

Di(N-methylbenzamido)dimethylsilane

In a stirring and distillation apparatus according to Example 1, 405.5 g of N-methylbenzamide (3 moles) were dissolved in 2400 g of anhydrous toluene at 65° C., and 625.5 g of sodium methanolate solution (25.9% strength, 3 moles) were run in. The azeotrope was removed under reduced pressure, in analogy with Examples 6 and 7, until methanol-free toluene distilled over. Then, while maintaining a bottom temperature of 70° C., 192.4 g of dimethyldichlorosilane (99.9% pure, 1.49 mole) were added dropwise (exothermic reaction—cooling), and the mixture was then stirred at this temperature for 3 h. After cooling the suspension, it was worked up as in the previous examples. 472 g (97% yield) of a virtually colourless, viscous liquid were obtained, and this formed colourless crystals at room temperature (melting point 54°-56° C.).

$^1$H NMR ($\sigma$ in ppm relative to TMS): a=0.53, b=2.90, c=7.37, d=7.90.

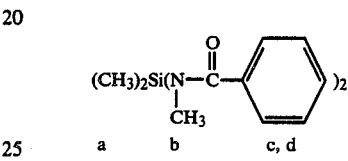

A 50% by weight solution of the substance thus prepared in toluene/butyl acetate (60:40 parts by weight) was prepared and used in the following recipe:
30 parts by weight of hydroxyl-terminated polydimethylsiloxane, viscosity about 50,000 mPas (25° C.)
20 parts by weight of unreactive polydimethylsiloxane, viscosity about 1500 mPas (25° C.)
4.5 parts by weight of chain extender prepared according to Example 8
4.5 parts by weight of crosslinker prepared according to Example 6
45 parts by weight of chalk
0.05 parts by weight of dibutyltin dilaurate.

A sheet prepaed in moist air cured completely and showed an elongation at break of about 900%.

What is claimed is:

1. A process for the preparation of amidosilanes of the formula

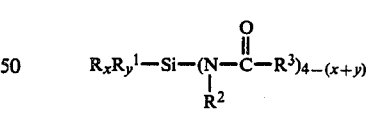

wherein
R is alkyl having 1 to 18 carbon atoms, cycloalkyl having 5–18 carbon atoms, alkenyl having 2 to 18 carbon atoms and aryl having 6 to 18 carbon atoms,
R$^1$ is alkoxy having 1 to 18 carbon atoms,
R$^2$ and R$^3$ each independently of one another are alkyl having 1 to 18 carbon atoms or aryl having 6 to 18 carbon atoms or R$^2$ or R$^3$ togethr are alkylene of 3 to 6 carbon atoms,
x is 1, 2 or 3,
y is 0, 1 or 2, with the sum of x and y being 1 to 3, which comprises reacting an alcohol-free suspension of alkali metal salts of organic amides and organosilanes wherein said salts of amides are of the formula

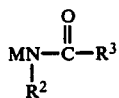

wherein M is an alkali metal and wherein said salts of amides are prepared by reacting a compound of the formula

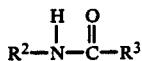

with alcoholic solution of an alkali metal alcoholate in inert organic solvents and then removing alcohol quantitatively from the reaction mixture by distillation, and said organosilanes are of the formula

wherein X is a halogen or a carboxylate moiety having 1 to 18 carbon atoms, with the reaction being carried out with exclusion of moisture in inert organic solvents.

2. A process according to claim 1 wherein toluene is the inert organic solvent.

3. A process according to claim 1 wherein the alcohol of the alcoholic solution corresponds to the alcoholate moiety in the alkali metal alcoholate.

4. A process according to claim 1 wherein methanolic sodium methanolate solution is the alcoholic alkali metal alcoholate solution.

5. A process according to claim 1 wherein the removal of the alcohol from the reaction mixture is by distillation under a pressure sufficiently reduced whereby the temperature in the distillation boiler is between 60° and 70° C.

6. A process according to claim 1 wherein the reaction of alcohol-free suspension of alkali metal salts or organic amides is with organochlorosilanes.

7. A process according to claim 6 wherein the reaction of alcohol-free suspensions of alkali metal salts of organic amides with organochlorosilanes is at temperatures between 60° and 80° C.

8. A process according to claim 1 wherein the amidosilane reaction product is worked-up by filtration to remove solid alkali metal halide by-product and the inert solvent is removed.

* * * * *